United States Patent [19]
Kofod et al.

[11] Patent Number: 6,022,723
[45] Date of Patent: Feb. 8, 2000

[54] ENZYME WITH β-(1-6)- ENDOGLUCANASE ACTIVITY

[75] Inventors: Lene Venke Kofod, Uggerløse; Lene Nonboe Andersen, Birkerod; Markus Sakari Kauppinen, Copenhagen N; Stephan Christgau, Gentofte; Henrik Dalbøge, Virum; Hans Sejr Olsen, Holte, all of Denmark

[73] Assignee: Novo Nordisk A/S, Bagsvaerd, Denmark

[21] Appl. No.: 09/040,699

[22] Filed: Mar. 18, 1998

Related U.S. Application Data

[62] Division of application No. 08/745,977, Nov. 8, 1996, Pat. No. 5,770,406, which is a continuation of application No. PCT/DK95/00189, May 11, 1995.

[30] Foreign Application Priority Data

May 11, 1994 [DK] Denmark .................. 0547/94

[51] Int. Cl.[7] ................ C12N 9/24; C12N 1/20; C12N 1/14; C12N 1/00; C07N 21/04
[52] U.S. Cl. ............... 435/200; 435/252.3; 435/254.11; 435/254.3; 435/256.1; 435/256.3; 435/256.5; 435/256.7; 435/320.1; 435/945; 536/23.2
[58] Field of Search ................ 435/200, 320.1, 435/252.3, 254.3, 254.11, 256.1, 256.3, 256.5, 256.7, 945; 536/23.2

[56] References Cited

FOREIGN PATENT DOCUMENTS

WO 94/07998  4/1994  WIPO .

OTHER PUBLICATIONS

Mulenga, D.K. et al., Microbios, vol. 10, pp. 143–154 (1994).
Schep, G.P. et al., Biochem. J., vol. 223, pp. 707–714 (1984).
Martin, D.F. et al., Applied and Environ. Microbio., vol. 40, No. 6, pp. 1136–1138 (1980).
Dobourdieu, D. et al., Carbohydrate Research, vol. 144, pp. 277–287 (1985).
Pitson, S.M. et al., Enzyme Microb. Technol., vol. 15, pp. 178–192 (1993).

*Primary Examiner*—Ponnathapu Achutamurthy
*Assistant Examiner*—Elizabeth Slobodyansky
*Attorney, Agent, or Firm*—Steve T. Zelson; Valeta Gregg

[57] ABSTRACT

The present invention relates to an enzyme with β-(1-6)-endoglucanase activity encoded by a DNA sequence, which DNA sequence a) comprises the DNA sequence shown in SEQ ID No. 3, or b) comprises an analogue of the DNA sequence shown in SEQ ID No. 3, which i) is homologous with the DNA sequences shown in or SEQ ID No. 3, and/or ii) hybridizes with the same oligonucleotide probe as the DNA sequence shown in SEQ ID No. 3, and/or iii) encodes a polypeptide which is homologous with the polypeptide encoded by a DNA sequence comprising the DNA sequence shown in SEQ ID No. 3, and/or iv) encodes a polypeptide which is immunologically reactive with an antibody raised against a purified β-(1-6)-glucanase shown in SEQ ID No. 4 derived from *Trichoderma harzianum*, CBS 243.71. The present invention also relates to a DNA construct encoding the enzyme, a method of producing the enzyme, an enzyme preparation containing the enzyme, and the use of the enzyme and enzyme preparation for the degradation or modification of β-glucan containing materials.

15 Claims, 3 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 332 base pairs
      (B) TYPE: nucleic acid
      (C) STRANDEDNESS: single
      (D) TOPOLOGY: linear    (ii) MOLECULE TYPE: cDNA    (xi) SEQUENCE DESCRIPTION: SEQ ID NO:1:

```
GATAATTCCT ACAGCTACCA TCAAGATGAA GTACTCCATC GTTGCTCCGG CCATTCTCGC      60

CGGCACCGCC TTTGCGTGGC TGCCTCAAGA CCGCGACCTG AAGGCCTTCA ACCAGACCGC     120

TCGTTTTGAG GAGCTTGGCA AGCGCTTTGA GCCTGCCCTT GCTTCTGGTA TCACCAAGAT     180

CCGTGGTGTC AACTTCGGTG GATGGCTTAT CAGCGAGCCA TGGATGATGT CCAATGAGTG     240

GAACAACAAC ATGGGCTGCA ACGGTGCTGC CTCTGAGTTC GATTGCATGC GCAACAACTA     300

CATGGGCAGC AAGCGTGCTA CCGGAAACAC CA                                   332
```

(2) INFORMATION FOR SEQ ID NO:2:

(i) SEQUENCE CHARACTERISTICS:
      (A) LENGTH: 367 base pairs
      (B) TYPE: nucleic acid
      (C) STRANDEDNESS: single
      (D) TOPOLOGY: linear    (ii) MOLECULE TYPE: cDNA    (xi) SEQUENCE DESCRIPTION: SEQ ID NO:2:

```
CGACTGGCAT GACGGAAACT TCTTCACCAA GTTCTTCACA GCTCAGCAGC AGCTGTATGA      60

GTCCCCTGGA ATGGACGGAT GGATCTACTG GACCTGGAAG ACCGAGCTAA ACGACCCCCG     120

ATGGACCTAC TCTTATGCTA CCTACCTCAA CTACATCCCA ACTAACGCCC GCCCTGCAGC     180

AGAACGTTTA CCAGGATGTC TGCGCTGGAT TCAGGTAAAT CACGAGTGGT TGCTCAACGA     240

CCAGCATCAC TTATTACATA CCACTTCAAA CTTGTATATT TTCTCGATGG ACATACTTTA     300

TTTAGACCTG AACACTACCT AGCCAACTTT AATTTACATA TAATGTGTTC TCAGTAAAAA     360

AAAAAAA                                                              367
```

(2) INFORMATION FOR SEQ ID NO:3:

(i) SEQUENCE CHARACTERISTICS:
        (A) LENGTH: 1290 base pairs
        (B) TYPE: nucleic acid
        (C) STRANDEDNESS: single
        (D) TOPOLOGY: linear     (ii) MOLECULE TYPE: cDNA     (ix) FEATURE:
        (A) NAME/KEY: CDS
        (B) LOCATION: 1..1287

(xi) SEQUENCE DESCRIPTION: SEQ ID NO:3:

```
ATG AAG TAC TCC ATC GTT GCT CCG GCC ATT CTC GCC GGC ACC GGC TTT        48
Met Lys Tyr Ser Ile Val Ala Pro Ala Ile Leu Ala Gly Thr Gly Phe
 1               5                  10                  15

GCG TGG CTG CCT CAA GAC CGC GAC CTG AAG GCC TTC AAC CAG ACC CCT        96
Ala Trp Leu Pro Gln Asp Arg Asp Leu Lys Ala Phe Asn Gln Thr Pro
                20                  25                  30

CGT TTT GAG GAG CTT GGC AAG CGC TTT GAG CCT GCC CTT GCT TCT GGT       144
Arg Phe Glu Glu Leu Gly Lys Arg Phe Glu Pro Ala Leu Ala Ser Gly
         35                  40                  45

ATC ACC AAG ATC CGT GGT GTC AAC TTC GGT GGA TGG CTT ATC AGC GAG       192
Ile Thr Lys Ile Arg Gly Val Asn Phe Gly Gly Trp Leu Ile Ser Glu
 50                  55                  60

CCA TGG ATG ATG TCC AAT GAG TGG AAC AAC AAC ATG GGC TGC AAC GGT       240
Pro Trp Met Met Ser Asn Glu Trp Asn Asn Asn Met Gly Cys Asn Gly
 65                  70                  75                  80

GCT GCC TCT GAG TTC GAT TGC ATG CGC AAC AAC TAC ATG GGC AGC AAG       288
Ala Ala Ser Glu Phe Asp Cys Met Arg Asn Asn Tyr Met Gly Ser Lys
                 85                  90                  95

CGT GCT ACC GGA AAC ACC AAG TTC CAG AAC CAC TAC AGG GAC TGG ATT       336
Arg Ala Thr Gly Asn Thr Lys Phe Gln Asn His Tyr Arg Asp Trp Ile
                100                 105                 110

AAC CCC GCC ACC GTT CAG TCT GTT CAC GAT GTC GGC TTG AAC ACT ATC       384
Asn Pro Ala Thr Val Gln Ser Val His Asp Val Gly Leu Asn Thr Ile
            115                 120                 125

CGT ATC CCC ATC GGC TAC TGG TCC TAC AAC GCC ATT GTC GAC ACG GCT       432
Arg Ile Pro Ile Gly Tyr Trp Ser Tyr Asn Ala Ile Val Asp Thr Ala
130                 135                 140

AGC GAG CCG TTT GCT GAT GGC AAC CTC CAG CTT CCG TAC CTT GAT GCT       480
Ser Glu Pro Phe Ala Asp Gly Asn Leu Gln Leu Pro Tyr Leu Asp Ala
145                 150                 155                 160

GTT GTT CAG AAG GCC GCT GAT CTC GGA ATC TAC GTC ATC ATT GAT CTT       528
Val Val Gln Lys Ala Ala Asp Leu Gly Ile Tyr Val Ile Ile Asp Leu
                165                 170                 175

CAC GGC GCC CCT GGT GGT CAG CAA CAG GAC GCC TTT ACC GGC CAG AAC       576
His Gly Ala Pro Gly Gly Gln Gln Gln Asp Ala Phe Thr Gly Gln Asn
            180                 185                 190

CCC AAC CCC GCC GGT TTC TAC AAC ACC TAC GAC TAT GGT CGT GCT GAG       624
Pro Asn Pro Ala Gly Phe Tyr Asn Thr Tyr Asp Tyr Gly Arg Ala Glu
        195                 200                 205

AAG TGG CTG TCT TGG ATG ACA AAC CGC ATC CAC ACC AAC CCT GCC TAC       672
Lys Trp Leu Ser Trp Met Thr Asn Arg Ile His Thr Asn Pro Ala Tyr
210                 215                 220

TCG ACT GTT GGT ATG ATT GAG GTT CTC AAC GAG CCT GTC TCC AGA CAC       720
Ser Thr Val Gly Met Ile Glu Val Leu Asn Glu Pro Val Ser Arg His
225                 230                 235                 240

GAT GGA GGT GGT CGC TAC CCT GCT CCT GGC CAG GAC CCA AGC ATG GTC       768
Asp Gly Gly Gly Arg Tyr Pro Ala Pro Gly Gln Asp Pro Ser Met Val
```

| | | | | | | | | | | | | | | |
|---|---|---|---|---|---|---|---|---|---|---|---|---|---|---|
| | | 245 | | | | 250 | | | | | 255 | | | |
| CAG | ACC | TAC | TAC | CCC | GGC | GCC | CTC | AAG | GCT | GTT | CGT | GAT | GCC | GAG | GCT | 816 |
| Gln | Thr | Tyr | Tyr | Pro | Gly | Ala | Leu | Lys | Ala | Val | Arg | Asp | Ala | Glu | Ala |
| | | 260 | | | | 265 | | | | 270 | | | | | |
| GCG | CTG | AAC | GTC | CCA | AGC | AAC | AAG | AAG | CTG | CAC | GTG | CAG | TTC | ATG | TCC | 864 |
| Ala | Leu | Asn | Val | Pro | Ser | Asn | Lys | Lys | Leu | His | Val | Gln | Phe | Met | Ser |
| | | 275 | | | | 280 | | | | 285 | | | | | |
| AGC | AAG | TGG | GAT | TCT | GGT | GAT | CCT | CGC | AGC | AAC | GCC | GCC | GTC | AAG | AAC | 912 |
| Ser | Lys | Trp | Asp | Ser | Gly | Asp | Pro | Arg | Ser | Asn | Ala | Ala | Val | Lys | Asn |
| | 290 | | | | | 295 | | | | 300 | | | | | |
| GAC | CCC | ATG | GTT | GGC | TTT | GAC | GAC | CAC | AAC | TAC | ATT | GGC | TTT | GCC | CTC | 960 |
| Asp | Pro | Met | Val | Gly | Phe | Asp | Asp | His | Asn | Tyr | Ile | Gly | Phe | Ala | Leu |
| 305 | | | | 310 | | | | 315 | | | | | 320 | | |
| CAG | AAC | ACT | GGC | GAC | CAG | TAC | TCT | CTC | ATG | CAC | AGT | GCC | TGC | ACT | GAC | 1008 |
| Gln | Asn | Thr | Gly | Asp | Gln | Tyr | Ser | Leu | Met | His | Ser | Ala | Cys | Thr | Asp |
| | | | 325 | | | | | 330 | | | | 335 | | | |
| TCT | CGT | GTC | GTG | AGC | GGC | CAG | GAC | TTT | GCC | ATC | ACT | GGC | GAG | TGG | AGC | 1056 |
| Ser | Arg | Val | Val | Ser | Gly | Gln | Asp | Phe | Ala | Ile | Thr | Gly | Glu | Trp | Ser |
| | | 340 | | | | | 345 | | | | 350 | | | | |
| ATG | ACT | TCT | GGT | GCC | GAC | TGG | CAT | GAC | GGA | AAC | TTC | TTC | ACC | AAG | TTC | 1104 |
| Met | Thr | Ser | Gly | Ala | Asp | Trp | His | Asp | Gly | Asn | Phe | Phe | Thr | Lys | Phe |
| | 355 | | | | 360 | | | | | 365 | | | | | |
| TTC | ACA | GCT | CAG | CAG | CAG | CTG | TAT | GAG | TCC | CCT | GGA | ATG | GAC | GGA | TGG | 1152 |
| Phe | Thr | Ala | Gln | Gln | Gln | Leu | Tyr | Glu | Ser | Pro | Gly | Met | Asp | Gly | Trp |
| 370 | | | | 375 | | | | | 380 | | | | | | |
| ATC | TAC | TGG | ACC | TGG | AAG | ACC | GAG | CTA | AAC | GAC | CCC | CGA | TGG | ACC | TAC | 1200 |
| Ile | Tyr | Trp | Thr | Trp | Lys | Thr | Glu | Leu | Asn | Asp | Pro | Arg | Trp | Thr | Tyr |
| 385 | | | | 390 | | | | 395 | | | | | | 400 | |
| TCT | TAT | GCT | ACC | TAC | CTC | AAC | TAC | ATC | CCA | ACT | AAC | GCC | GCT | GCC | CTG | 1248 |
| Ser | Tyr | Ala | Thr | Tyr | Leu | Asn | Tyr | Ile | Pro | Thr | Asn | Ala | Ala | Ala | Leu |
| | | | 405 | | | | 410 | | | | 415 | | | | |
| CAG | CAG | AAC | GTT | TAC | CAG | GAT | GTC | TGC | GCT | GGA | TTC | AGG | TAA | | | 1290 |
| Gln | Gln | Asn | Val | Tyr | Gln | Asp | Val | Cys | Ala | Gly | Phe | Arg |
| | 420 | | | | | 425 | | | | | | | | | |

(2) INFORMATION FOR SEQ ID NO:4:

(i) SEQUENCE CHARACTERISTICS:
        (A) LENGTH: 429 amino acids
        (B) TYPE: amino acid
        (D) TOPOLOGY: linear     (ii) MOLECULE TYPE: protein     (xi) SEQUENCE DESCRIPTION: SEQ ID NO:4:

| Met | Lys | Tyr | Ser | Ile | Val | Ala | Pro | Ala | Ile | Leu | Ala | Gly | Thr | Gly | Phe |
|---|---|---|---|---|---|---|---|---|---|---|---|---|---|---|---|
| 1 | | | | 5 | | | | | 10 | | | | | 15 | |
| Ala | Trp | Leu | Pro | Gln | Asp | Arg | Asp | Leu | Lys | Ala | Phe | Asn | Gln | Thr | Pro |
| | | | 20 | | | | | 25 | | | | | 30 | | |
| Arg | Phe | Glu | Glu | Leu | Gly | Lys | Arg | Phe | Glu | Pro | Ala | Leu | Ala | Ser | Gly |
| | | 35 | | | | | 40 | | | | | 45 | | | |
| Ile | Thr | Lys | Ile | Arg | Gly | Val | Asn | Phe | Gly | Gly | Trp | Leu | Ile | Ser | Glu |
| | 50 | | | | | 55 | | | | | 60 | | | | |
| Pro | Trp | Met | Met | Ser | Asn | Glu | Trp | Asn | Asn | Met | Gly | Cys | Asn | Gly |
| 65 | | | | | 70 | | | | | 75 | | | | | 80 |
| Ala | Ala | Ser | Glu | Phe | Asp | Cys | Met | Arg | Asn | Asn | Tyr | Met | Gly | Ser | Lys |
| | | | | 85 | | | | | 90 | | | | | 95 | |
| Arg | Ala | Thr | Gly | Asn | Thr | Lys | Phe | Gln | Asn | His | Tyr | Arg | Asp | Trp | Ile |
| | | | 100 | | | | | 105 | | | | | 110 | | |

```
                                   -continued

Asn Pro Ala Thr Val Gln Ser Val His Asp Val Gly Leu Asn Thr Ile
        115                 120                 125

Arg Ile Pro Ile Gly Tyr Trp Ser Tyr Asn Ala Ile Val Asp Thr Ala
        130                 135                 140

Ser Glu Pro Phe Ala Asp Gly Asn Leu Gln Leu Pro Tyr Leu Asp Ala
145                 150                 155                 160

Val Val Gln Lys Ala Ala Asp Leu Gly Ile Tyr Val Ile Ile Asp Leu
                165                 170                 175

His Gly Ala Pro Gly Gly Gln Gln Gln Asp Ala Phe Thr Gly Gln Asn
                180                 185                 190

Pro Asn Pro Ala Gly Phe Tyr Asn Thr Tyr Asp Tyr Gly Arg Ala Glu
        195                 200                 205

Lys Trp Leu Ser Trp Met Thr Asn Arg Ile His Thr Asn Pro Ala Tyr
        210                 215                 220

Ser Thr Val Gly Met Ile Glu Val Leu Asn Glu Pro Val Ser Arg His
225                 230                 235                 240

Asp Gly Gly Gly Arg Tyr Pro Ala Pro Gly Gln Asp Pro Ser Met Val
                245                 250                 255

Gln Thr Tyr Tyr Pro Gly Ala Leu Lys Ala Val Arg Asp Ala Glu Ala
                260                 265                 270

Ala Leu Asn Val Pro Ser Asn Lys Lys Leu His Val Gln Phe Met Ser
        275                 280                 285

Ser Lys Trp Asp Ser Gly Asp Pro Arg Ser Asn Ala Ala Val Lys Asn
        290                 295                 300

Asp Pro Met Val Gly Phe Asp Asp His Asn Tyr Ile Gly Phe Ala Leu
305                 310                 315                 320

Gln Asn Thr Gly Asp Gln Tyr Ser Leu Met His Ser Ala Cys Thr Asp
                325                 330                 335

Ser Arg Val Val Ser Gly Gln Asp Phe Ala Ile Thr Gly Glu Trp Ser
                340                 345                 350

Met Thr Ser Gly Ala Asp Trp His Asp Gly Asn Phe Phe Thr Lys Phe
        355                 360                 365

Phe Thr Ala Gln Gln Gln Leu Tyr Glu Ser Pro Gly Met Asp Gly Trp
        370                 375                 380

Ile Tyr Trp Thr Trp Lys Thr Glu Leu Asn Asp Pro Arg Trp Thr Tyr
385                 390                 395                 400

Ser Tyr Ala Thr Tyr Leu Asn Tyr Ile Pro Thr Asn Ala Ala Ala Leu
                405                 410                 415

Gln Gln Asn Val Tyr Gln Asp Val Cys Ala Gly Phe Arg
                420                 425
```

ENZYME WITH β-(1-6)- ENDOGLUCANASE ACTIVITY

CROSS-REFERENCE TO RELATED APPLICATIONS

This application is a divisional of application Ser. No. 08/745,977 filed on Nov. 8, 1996 now U.S. Pat. No. 5,770,406, which is a continuation of PCT/DK95/00189 filed on May 11, 1995 and claims priority under 35 U.S.C. 119 of Danish application serial no. 0547/94 filed May 11, 1994, the contents of which are fully incorporated herein by reference.

FIELD OF INVENTION

The present invention relates to an enzyme with β-(1-6)-endoglucanase activity, a DNA construct encoding the enzyme, a method of producing the enzyme, an enzyme preparation containing the enzyme, and the use of the enzyme and enzyme preparation for the degradation or modification of β-glucan containing materials.

BACKGROUND OF THE INVENTION

β-(1-6)-endoglucanases (E.C. 3.2.1.75) are enzymes which catalyses the cleavage of β-(1-6) linkages in β-glucan, a major component of the cell walls of fungal (including yeast) cells. These enzymes are also referred to as pustulanases due to their capability of degrading pustulan.

Cell walls of fungal microorganisms such as yeasts and fungi are complex structures which, in addition to β-glucan, comprise a number of other components. For instance, yeast cell walls comprises a protein-mannan complex layer in addition to a glucan layer (Andrews and Asenjo, 1987), and cell walls of filamentous fungi additionally comprise varying amounts of chitin and chitosan (cf. Hudson, H. J., 1986).

It is well-known that microorganisms produce a number of valuable products such as colorants, flavorants, vitamins, the isolation of which is desirable. The isolation of intracellularly produced products requires that the cell walls of the microbial producers be ruptured or lysed.

Because of the complex composition of microbial cell walls, the rupture or lysis of cell walls has traditionally been carried out by rather vigorous treatments involving the use of strong chemicals and/or mechanical means.

Enzymatic lysis and disruption of microbial cells have been suggested as a desirable alternative to chemical or mechanical rupture in the production of yeast extracts or other intracellularly produced products (Andrew and Asenjo (1987), Phaff (1977)). Furthermore, enzymatic lysis has been suggested for use in the preparation of protoplast from fungi or yeasts (Hamlyn et al., 1981). A number of commercially available enzyme preparations useful in the enzymatic lysis of yeast and fungal cells are available. Such products normally comprise multiple enzymatic activities, e.g. including β-(1-3)- and/or β-(1-6)-glucanase, protease, chitinase, mannanase and other enzymes capable of cleaving cell wall components.

Dubourdieu et al., (1985) (Carbohydrate Research, 144, 277–287), have investigated an industrial enzyme preparation (Novo Industri A/S) derived from a strain of *Trichoderma harzianum* which, among other glucanases, comprises a β-(1-6)-endoglucanase.

According to Pitson et al., (1993), filamentous fungi such as *Penicillium brefeldianum, Trichoderma harzianum* and yeasts such as *Saccharomyces cerevisiae* are known to produce enzymes exhibiting β-(1-6)-endoglucanase activity.

It would be desirable to be able to improve the cell wall degrading or modifying capability of such enzyme preparations and further to be able to more specifically control the degradation or modification of specific cell wall components.

SUMMARY OF THE INVENTION

The present inventors have now surprisingly by the use of an new assay succeeded in isolating and characterizing a DNA sequence which encodes an enzyme exhibiting β-(1-6)-glucanase activity, thereby making it possible to prepare single-component β-(1-6)-glucanases.

Accordingly, in a first aspect the invention relates to a DNA construct comprising a DNA sequence encoding an enzyme exhibiting β-(1-6)-glucanase activity, which DNA sequence a) comprises the DNA sequence shown in SEQ ID No. 3, or b) comprises an analogue of the DNA sequence shown in SEQ ID No. 3, which i) is homologous with the DNA sequence shown in SEQ ID No. 3, and/or ii) hybridizes with the same oligonucleotide probe as the DNA sequence shown in SEQ ID No. 3, and/or iii) encodes a polypeptide which is homologous with the polypeptide encoded by a DNA sequence shown in SEQ ID No. 3, and/or iv) encodes a polypeptide which is immunologically reactive with an antibody raised against a purified β-(1-6)-glucanase shown in SEQ ID No. 4 derived from *Trichoderma harzianum,* CBS 243.71.

In the present context, the "analogue" of the DNA sequence shown in SEQ ID No. 3 is intended to indicate any DNA sequence encoding an enzyme exhibiting β-(1-6)-glucanase activity, which has the properties i)–iv) above. Typically, the analogous DNA sequence is isolated from another or related (e.g. the same) organism known or contemplated to produce the enzyme with β-(1-6)-glucanase activity on the basis of the DNA sequence shown in SEQ ID No. 3, or any of the partial DNA sequences shown in SEQ ID Nos. 1 or 2, e.g. using the procedures described herein, or is constructed on the basis of the DNA sequence shown in SEQ ID No. 3, or any of the DNA sequences shown in SEQ ID Nos. 1 or 2, e.g. by introduction of nucleotide substitutions which do not give rise to another amino acid sequence of the β-(1-6)-glucanase encoded by the DNA sequence, but which correspond to the codon usage of the host organism intended for production of the enzyme, or by introduction of nucleotide substitutions which do give rise to a different amino acid sequence and therefore, possibly, a different protein structure which might give rise to a β-(1-6)-glucanase mutant with different properties than the native enzyme. Other examples of possible modifications are insertion of one or more nucleotides into the sequence, addition of one or more nucleotides at either end of the sequence, or deletion of one or more nucleotides at either end or within the sequence. For instance, the analogous DNA sequence may be a subsequence of the DNA sequence shown in SEQ ID No. 3, or any of the DNA sequences shown in SEQ ID Nos. 1 or 2.

It will be understood that the DNA sequence shown in SEQ ID Nos. 1 or 2 are partial sequences which may be used for isolating the entire DNA sequence encoding the enzyme with β-(1-6)-glucanase activity. The term "analogue" is intended to include said entire DNA sequence, which comprises one or more of the partial sequences shown in SEQ ID Nos. 1 or 2 or parts thereof.

The hybridization referred to in i) above is intended to indicate that the analogous DNA sequence hybridizes to the same probe as the DNA sequence encoding the β-(1-6)-glucanase enzyme under certain specified conditions which are described in detail in the Materials and Methods section hereinafter. Normally, the analogous DNA sequence is highly homologous to the DNA sequence such as at least 70% homologous to any of the sequences shown above encoding a β-(1-6)-glucanase of the invention, such as at least 75%, at least 80%, at least 85%, at least 90% or even at least 95% homologous to any of the sequences shown above.

The degree of homology referred to in i) above is determined as the degree of identity between the two sequences indicating a derivation of the first sequence from the second. The homology may suitably be determined by means of computer programs known in the art. Typically, the DNA sequence exhibits a degree of identity of at least 70%, such as at least 80% or 90% with the DNA construct comprising the entire DNA sequence shown in SEQ ID No. 3, or the partial DNA sequences SEQ ID Nos. 1 and/or 2.

The degree of homology referred to in iii) above is determined as the degree of identity between the two sequences indicating a derivation of the first sequence from the second. The homology may suitably be determined by means of computer programs known in the art. Typically, the polypeptide encoded by an analogous DNA sequence exhibits a degree of homology of at least 70%, such as at least 80% or 90% with the enzyme encoded by a DNA construct comprising the entire DNA sequence shown in SEQ ID No. 3, or the partial DNA sequences SEQ ID Nos. 1 and/or 2.

The term "derived from" in connection with property iii) above is intended not only to indicate a β-(1-6)-glucanase produced by strain CBS 243.71, but also a β-(1-6)-glucanase encoded by a DNA sequence isolated from strain CBS 243.71 and produced in a host organism transformed with said DNA sequence. The immunological reactivity may be determined by the method described in the Materials and Methods section below.

In further aspects the invention relates to an expression vector harboring a DNA construct of the invention, a cell comprising the DNA construct or expression vector and a method of producing an enzyme exhibiting β-(1-6)-glucanase activity which method comprises culturing said cell under conditions permitting the production of the enzyme, and recovering the enzyme from the culture.

In a still further aspect the invention relates to an enzyme exhibiting β-(1-6)-glucanase activity, which enzyme a) is encoded by a DNA construct of the invention b) produced by the method of the invention, and/or c) is immunologically reactive with an antibody raised against a purified β-(1-6)-glucanase shown in SEQ ID No. 4 derived from Trichoderma harzianum, CBS 243.71.

Said isolated enzyme of the invention has been characterized as described in the examples below. For instance it was found that the apparent molecular weight ($M_w$), determined by SDS-PAGE electrophoresis, is about 50 kDa. Further the apparent pI (isoelectric point) was found to be about 5,6.

Also kinetic parameters and the specific activity were determined. The specific activity of the isolated pustalanase at 30° C., pH 5.0, was around 100 U/mg enzyme, and Km was around 0.3% pustulan.

Figure 1:
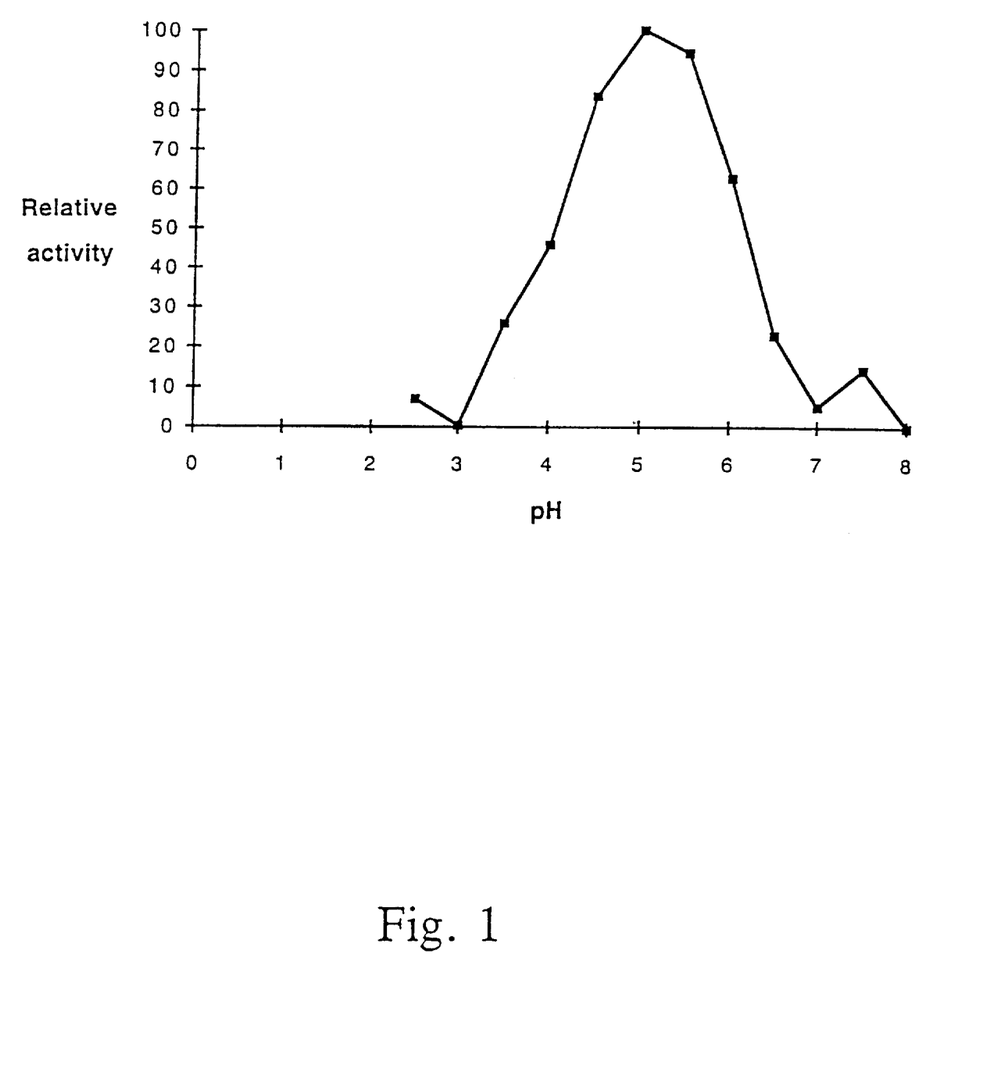
FIG. 1 shows the relative activity of pustulanase as a function of pH at 30° C.

Further, it was seen that the pustulanase of the invention has more that 40% activity between pH 4.0 and 6.0 and optimal activity at about pH 5.0 (see FIG. 1). The relative enzyme activity was found to be 40% at 50° C. and optimal at 30–40° C. (see FIG. 2).

The enzyme was shown to depolymerize β-(1-6)-glucan (pustulan) in accordance with the definition of β-(1-6)-glucanases (E.C. 3.2.1.75).

In a still further aspect, the present invention relates to an enzyme preparation useful for the degradation or modification of β-glucan containing materials, in particular microbial cell wall material, said preparation being enriched in an enzyme exhibiting β-(1-6)-glucanase activity as described above.

DETAILED DESCRIPTION OF THE INVENTION

The DNA sequence of the invention encoding an enzyme exhibiting β-(1-6)-glucanase activity may be isolated by a general method involving cloning, in suitable vectors, a DNA library from Trichoderma harzianum, transforming suitable yeast host cells with said vectors, culturing the host cells under suitable conditions to express any enzyme of interest encoded by a clone in the DNA library, screening for positive clones by determining any β-(1-6)-glucanase activity of the enzyme produced by such clones, and isolating the enzyme encoding DNA from such clones.

The general method is further disclosed in WO 93/11249 which is hereby incorporated by reference. A more detailed description of the screening method is given in Example 1 below.

The DNA sequence coding for the enzyme may for instance be isolated by screening a cDNA library of Trichoderma harzianum, e.g. strain CBS 243.71, publicly available from the Centraalbureau voor Schimmelcultures, Delft, NL, and selecting for clones expressing the appropriate enzyme activity (i.e. β-(1-6)-glucanase activity as defined by the ability of the enzyme to hydrolyze β-(1-6)-glucan bonds of a suitable substrate such as DCL-pustulan, cf. the Materials and Methods section hereinafter. The appropriate DNA sequence may then be isolated from the clone by standard procedures, e.g. as described in Example 1.

It is expected that a DNA sequence coding for a homologous enzyme, i.e. an analogous DNA sequence, is obtainable from other microorganisms. For instance, the DNA sequence may be derived by similarly screening a cDNA library of another microorganism, in particular a fungus, such as a strum of an Aspergillus sp., in particular a strain of A. aculeatus or A. niger, a strain of another Trichoderma sp., in particular a strain of T. reesie, T. viride, T. longibrachiatum or T. koningii or a strain of a Fusarium sp., in particular a strain of F. oxysporum, or a strain of a Humicola sp., or a strain of Acremonium sp., or a strain of a Penicillium sp.

Alternatively, the DNA coding for an β-(1-6)-glucanase of the invention may, in accordance with well-known procedures, conveniently be isolated from DNA from any of the above mentioned organisms by use of synthetic oligonucleotide probes prepared on the basis of a DNA sequence disclosed herein. For instance, a suitable oligonucleotide probe may be prepared on the basis of the full length nucleotide sequence shown in SEQ ID No. 3, or any of the partial nucleotide sequences shown in SEQ ID Nos. 1 and 2.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the $\beta$-(1-6)-glucanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the $\beta$-(1-6)-glucanase, the promoter and the terminator, respectively, and to insert them into suitable vectors are well known to persons skilled in the art (cf., for instance, Sambrook et al., *Molecular Cloning, A Laboratory Manual*, Cold Spring Harbor, N.Y., 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Nordisk A/S), the contents of which are hereby incorporated by reference. The host cell may also be a yeast cell, e.g. a strain of Saccharomyces sp., in particular *Saccharomyces cerevisiae, Saccharomyces kluyveri* or *Saccharomyces uvarum*, a strain of Schizosaccharomyces sp., such as *Schizosaccharomyces pombe*, a strain of Hansenula sp. Pichia sp., Yarrowia sp. such as *Yarrowia lipolytica*, or Kluyveromyces sp. such as *Kluyveromyces lactis*, or Acremonium sp.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed $\beta$-(1-6)-glucanase may conveniently be secreted into the culture medium and may be recovered there from by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

In a still further aspect, the present invention relates to an enzyme preparation useful for the modification or degradation of $\beta$-glucan containing materials, said preparation being enriched in an enzyme exhibiting $\beta$-(1-6)-glucanase activity as described above.

The enzyme preparation having been enriched with an enzyme of the invention may e.g. be an enzyme preparation comprising multiple enzymatic activities, in particular an enzyme preparation comprising different enzyme activities required for the modification or degradation of microbial cell walls. Examples of such enzyme preparation includes lytic enzyme systems, in particular of microbial (fungal or bacterial) origin, e.g. derived from a strain of Trichoderma, such as *Trichoderma harzianum, Trichoderma viride* or *Trichoderma reesie*, a strain of Oerskovia sp., such as *Oerskovia xanthineolytica*, a strain of Arthrobacter sp. such as *Arthrobacter luteus*, a strain of Rhizoctonia sp. or Cytophaga sp., a strain of a Staphylococcus sp., or a strain of Streptomyces sp. Commercially available enzyme preparations which may conveniently be boosted with an enzyme of the invention includes Novozyme® 234 and Cereflo® 200L, Glucanex®, all available from Novo Nordisk A/S, Denmark, Cellulase (available from Merck), Cellulase CP and Cellulase CT (both available from Sturge), and/or Chitinase (available from Sigma).

In the present context, the term "enriched" is intended to indicate that the $\beta$-(1-6)-glucanase activity of the enzyme preparation has been increased, e.g. with an enrichment factor of at least 1.1, conveniently due to addition of an enzyme of the invention prepared by the method described above.

Alternatively, the enzyme preparation enriched with an enzyme exhibiting $\beta$-(1-6)-glucanase activity may be one which comprises an enzyme of the invention as the major enzymatic component, e.g. a mono-component enzyme preparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

The enzyme preparation of the invention may, in addition to a $\beta$-(1-6)-glucanase of the invention, contain one or more other cell wall degrading enzymes, for instance those with cellulolytic, mannanolytic, chitinolytic or proteolytic activities such as cellulase, endoglucanase, $\beta$-(1-3)-glucanase, mannanase, endo- or exo- chitinase, protease, $\alpha$- or $\beta$-mannosidase or mutanase. The additional enzyme(s) may be producible by means of a microorganism belonging to the genus Aspergillus, preferably *Aspergillus niger, Aspergillus aculeatus, Aspergillus awamori* or *Aspergillus oryzae*, or Trichoderma or any of the microorganisms mentioned above in connection with the commercially available enzyme preparations.

Examples are given below of preferred uses of the enzyme preparation of the invention. The dosage of the enzyme preparation of the invention and other conditions under which the preparation is used may be determined on the basis of methods known in the art.

The enzyme preparation according to the invention is preferably used as an agent for degradation or modification of $\beta$-glucan containing material such as microbial cell walls. In particular, the enzyme preparation of the invention may be used for rupturing or lysing cell walls of microorganisms thereby enabling recovery of desirable products produced by the microorganism.

It will be understood that the specific composition of the enzyme preparation to be used should be adapted to the composition of the cell wall to be ruptured or lysed. For instance, yeast cell walls have been found to comprise two main layers, an outer layer of protein-mannan complex and an inner glucan layer. In order to efficiently rupturing the cell wall of yeast it is desirable that the enzyme preparation comprises at least protease, mannanase, chitinase and β-glucanase activity.

The extract recovered after rupture of the microbial cell walls normally comprises a number of different components, such as vitamins, colorants, flavorants, emulsifiers and stabilizers. Extracts obtained from rupture of yeast, i.e. yeast extracts, are used as such, e.g. for food or feed applications—or components thereof may be recovered and optionally further processed.

Examples of such products include emulsifiers, stabilizers, vitamins, colorants (e.g. carotenoids, Q-10 and astaxathin), enzymes, proteins and flavor components or flavor enhancers (e.g. MSG, 5'-GMP and 5'-IMP). The products to be recovered may be inherent products of the microorganism in question, or may be products which the microorganism has been constructed to produce, e.g. recombinant products.

Further, the pustulanase of the invention can be used for extracting mannan protein from the outer layer of yeast cell walls, such the cell wall of *Saccharomyces cerevisiae*. Manno-protein can be used as an effective bioemulsifier.

In addition, the enzyme preparation of the invention may be used in the production of protoplast from yeasts (e.g. of Saccharomyces sp. or Schizosaccharomyces sp.) or from fungi (e.g. Aspergillus sp. or Penicillium sp.). Preparation and regeneration of protoplast from such organisms are important in fusion, transformation and cloning studies. The production of protoplasts may be performed in accordance with methods known in the art.

In addition, the enzyme preparation of the invention may be used in the modification of β-glucans such as pustulan, and other β-glucans, with β-1-6-linkages.

The activity towards β-glucans, such as pustulan, makes the pustulanase of the invention and homologues thereof useful for improving the filterability in processes for making grape wine or press-juice.

The pustulanase of the invention improves the filterability by preventing growth of microorganisms, such as *Botrytis cinerea*, which may infect the grapes.

Also contemplated according to the invention is the use of pustulanase or enzyme preparation thereof as an active ingredient in cleaning compositions for dentures. The composition is capable of removing microorganisms from the surface of dentures.

Also the use in plaque removing compositions, in e.g. mouth washes is contemplated. Plaque are formed on the surface of teeth is composed mainly of polysaccharides. They stick to the surface of the teeth and the microorganisms present in the mouth. The pustulanase of the invention may in this context be use in combination with other glucanases such as mutanase and dextranase.

Also bioflims formed on the surface of e.g. contact lens cases can be removed by the action of glucanases, including the pustulanase of the invention.

Further molds on coatings may also be removed by the use of compositions comprising the pustulanase of the invention.

Also contemplated is the use of pustulanase as an antifungal agent.

In connection with removal of excess dye from textiles the pustulanase of the invention can also be used advantageously.

The invention is described in further detail in the following examples which are not in any way intended to limit the scope of the invention as claimed.

MATERIALS AND METHODS

Dyeing and crosslinking of pustulan (β-1-6-glucan)

DCL-pustulan was prepared using the following procedure: 2 g pustulan (Roth, Art. 6637) was dissolved in 100 ml of water and pH adjusted to 7. 1 g of dye (cibacron C2-R blau, Ciba Geigy) was added and the reaction mixture was heated to 50° C. 10 g $Na_2SO_4$ was added and stirring was continued at 50° C. for 40 minutes before addition of 1.5 g of $Na_3PO_4 \times 12H_2O$ and adjustment to pH 11 and stirring for additionally 1 hour. Dialysis against running water over night or precipitation with 400 ml of 96% ethanol and centrifugation ensured removal of dye in excess. The dyed pustulan was cross-linked by dissolving in 200 ml of water and adjustment of pH to 12 and addition of 10 ml of Divinylsulphon (Fluka) and 800 ml of 96% ethanol. The reaction proceeded for 60 minutes at room temperature and was stopped by neutralization and centrifugation. The sediment was resuspended in boiling water and centrifuged. The dyed, cross-linked pustulan (DCL-pustulan) was recovered as the sediment and used in the plate screening assay for pustulanases (β-1-6-glucanase).

Donor organism:

mRNA was isolated from *Trichoderma harzianum*, CBS 243.71, grown in a maize grits-containing fermentation medium with agitation to ensure sufficient aeration. Mycelia were harvested after 3–5 days' growth, immediately frozen in liquid nitrogen and stored at −80° C.

Yeast strains:

The *Saccharomyces cerevisiae* strain used was yNG231 (MAT alpha, leu2, ura3-52, his4-539, pep4-delta 1, cir+) or JG169 (MATα; ura 3-52; leu 2-3, 112; his 3-D200; pep 4-1137; prc1::HIS3; prb1:: LEU2; cir+).

Plasmids:

The expression plasmid pYHD17 containing the yeast TPI promoter was prepared from the commercially available plasmid pYES 2.0 (Invitrogen). The plasmid and the construction thereof is further described in WO 93/11249, the contents of which is hereby incorporated by reference.

The Aspergillus expression vector pHD414 is a derivative of the plasmid p775 (described in EP 238 023). The construction of pHD414 is further described in WO 93/11249.

Extraction of total RNA:

The total RNA was prepared by extraction with guanidinium thiocyanate followed by ultracentrifugation through a 5.7 M CsCl cushion essentially as described by Chirgwin et al., 1979 and in WO 94/14952.

Isolation of poly(A)$^+$RNA

The poly(A)$^+$ RNAs were isolated by oligo(dT)-cellulose affinity chromatography using the procedure described in WO 94/14952.

cDNA synthesis and modification

Double-stranded cDNA was synthesized from 5 µg of poly(A)$^+$ RNA by the RNase H method (Gubler & Hoffman 1983, Sambrook et al., 1989) using the hair-pin modification. The synthesis of double stranded cDNA was carried out as described earlier in WO 95/02044, except that 25 ng of random hexanucleotide primers (Gibco BRL, USA) were added to the first strand synthesis reaction mixture. After having been treated with Mung bean nuclease (Bethesda Research Laboratories), the ds cDNA was made blunt-ended with T4 DNA polymerase (Invitrogen) and the cDNA was ligated to non-palindromic BstX I adaptors, Invitrogen) in accordance with the manufacturers instructions.

Construction of cDNA libraries

The adapted, ds cDNA was recovered by centrifugation, washed in 70% EtOH and resuspended in 25 ml distilled water. Prior to large-scale library ligation, four test ligations were carried out in 10 μl of ligation buffer (same as above) each containing 1 μds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector (either pYES 2.0 vector Invitrogen or yHD13). The ligation reactions were performed by incubation at 16° C. for 12 h, heated at 70° C. for 5 min, and 1 μl of each ligation electroporated (200 Ω, 2.5 kV, 25 μF) to 40 μl competent E. coli 1061 cells (OD600=0.9 in 1 liter LB-broth, washed twice in cold distilled water, once in 20 ml of 10% glycerol, resuspended in 2 ml 10% glycerol). After addition of 1 ml SOC to each transformation mix, the cells were grown at 37° C. for 1 h, 50 μl plated on LB+ampicillin plates (100 μg/ml) and grown at 37° C. for 12 hours.

Using the optimal conditions a large-scale ligation was set up in 40 μl of ligation buffer containing 9 units of T4 ligase, and the reaction was incubated at 16° C. for 12 h. The ligation reaction was stopped by heating at 70° C. for 5 min, ethanol precipitated at –20° C. for 12 h, recovered by centrifugation and resuspended in 10 μl distilled water. One μl aliquots were transformed into electrocompetent E. coli 1061 cells using the same electroporation conditions as above, and the transformed cells were titered and the library plated on LB+ampicillin plates with 5000–7000 c.f.u./plate. To each plate was added 3 ml of medium. The bacteria were scraped off, 1 ml glycerol was added and stored at –80° C. as pools. The remaining 2 ml were used for DNA isolation. If the amount of DNA was insufficient to give the required number of yeast transformants, large scale DNA was prepared from 500 ml medium (TB) inoculated with 50 μl of –80° C. bacterial stock propagated overnight.

Construction of yeast libraries

To ensure that all the bacterial clones were tested in yeast, a number of yeast transformants 5 times larger than the number of bacterial clones in the original pools was set as the limit.

One μl aliquots of purified plasmid DNA (100 ng/μl) from individual pools were electroporated (200 Ω, 1.5 kV, 25 μF) into 40 μl competent S. cerevisiae JG 169 cells (OD600=1.5 in 500 ml YPD, washed twice in cold distilled water, once in cold 1 M sorbitol, resuspended in 0.5 ml 1 M sorbitol, Becker & Guarante, 1991). After addition of 1 ml 1 M cold sorbitol, 80 μl aliquots were plated on SC+glucose–uracil agar plates to give 250–400 c.f.u./plate and incubated at 30° C. for 3–5 days.

Identification of positive colonies

After 3–5 days of growth, the agar plates were replica plated onto several sets of SC+galactose–uricil agar plates. One set of plates containing DCL-pustulan was then incubated for 3–5 days at 30° C. to detect for β-(1-6)-glucanase activity. Positive colonies were identified as colonies surrounded by a blue halo.

Cells from enzyme-positive colonies were spread for single colony isolation on agar, and an enzyme-producing single colony was selected for each of the β-(1-6)-glucanase-producing colonies identified.

Characterization of positive clones

The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al., 1977) and the Sequenase® system (United States Biochemical).

Isolation of a cDNA gene for expression in Aspergillus

One or more β-(1-6)-glucanase-producing colonies was inoculated into 20 ml YPD broth in a 50 ml glass test tube. The tube was shaken for 2 days at 30° C. The cells were harvested by centrifugation for 10 min. at 3000 rpm.

The cells were resuspended in 1 ml 0.9 M sorbitol, 0.1 M EDTA, pH 7.5. The pellet was transferred to an Eppendorf tube, and spun for 30 seconds at full speed. The cells were resuspended in 0.4 ml 0.9 M sorbitol, 0.1 M EDTA, 14 mM β-mercaptoethanol. 100 μl 2 mg/ml Zymolase was added, and the suspension was incubated at 37° C. for 30 minutes and spun for 30 seconds. The pellet (spheroplasts) was resuspended in 0.4 ml TE. 90 μl of (1.5 ml 0.5 M EDTA pH 8.0, 0.6 ml 2 M Tris-Cl pH 8.0, 0.6 ml 10% SDS) was added, and the suspension was incubated at 65° C. for 30 minutes. 80 μl 5 M KOAc was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% EtOH, spun for 30 seconds and dried at room temperature. The pellet was resuspended in 50 μl TE and spun for 15 minutes. The supernatant was transferred to a fresh tube. 2.5 μl 10 mg/ml RNase was added, followed by incubation at 37° C. for 30 minutes and addition of 500 μl isopropanol with gentle mixing. The mixture was spun for 30 seconds, and the supernatant was removed. The pellet was rinsed with cold 96% EtOH and dried at room temperature. The DNA was dissolved in 50 μl water to a final concentration of approximately 100 μg/ml.

The DNA was transformed into E. coli by standard procedures. Plasmid DNA was isolated from E. coli using standard procedures, and analyzed by restriction enzyme analysis. The cDNA insert was excised using appropriate restriction enzymes and ligated into an Aspergillus expression vector.

Transformation of Aspergillus oryzae or Aspergillus niger (general procedure)

100 ml of YPD (Sherman et al., Methods in Yeast Genetics, Cold Spring Harbor Laboratory, 1981) is inoculated with spores of A. oryzae or A. niger and incubated with shaking at 37° C. for about 2 days. The mycelium is harvested by filtration through miracloth and washed with 200 ml of 0.6 M MgSO$_4$. The mycelium is suspended in 15 ml of 1.2 M MgSO$_4$. 10 mM NaH$_2$PO$_4$, pH=5.8. The suspension is cooled on ice and 1 ml of buffer containing 120 mg of Novozym® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6 M sorbitol, 100 mM Tris-HCl, pH=7.0. Centrifigation is performed for 15 minutes at 100 g and the protoplasts are collected from the top of the MgSO$_4$ cushion. 2 volumes of STC (1.2 M sorbitol, 10 mM Tris-HCl, pH=7.5. 10 mM CaCl$_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC.

100 μl of protoplast suspension is mixed with 5–25 μg of the appropriate DNA in 10 μl of STC. Protoplasts are mixed with p3SR2 (an A. nidulans amdS gene carrying plasmid). The mixture is left at room temperature for 25 minutes. 0.2 ml of 60% PEG 4000 (BDH 29576). 10 mM $CaCl_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on the appropriate plates. Protoplasts are spread on minimal plates (Cove Biochem.Biophys.Acta 113 (1966) 51–56) containing 1.0 M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of A. oryzae transformants

Each of the transformants were inoculated on FG-4 agar containing DCL-pustulan. After 5 days of incubation at 30° C. the β-(1-6)-glucanase activity was identified as described above.

Hybridization conditions (to be used in evaluating property i) of the DNA construct of the invention)

Suitable conditions for determining hybridization between an oligonucleotide probe and an "analogous" DNA sequence involves presoaking of the filter containing the DNA sequences to hybridize in 5×SSC and prehybridizing the sequences for 1 h at ~40° C. in a solution of 5×SSC, 5×Denhardt's solution, 50 mM sodium phosphate, pH 6.8, and 50 μg of denatured sonicated calf thymus DNA, followed by hybridization in the same solution supplemented with 50 μCi 32-P-dCTP labelled probe for 18 h at ~40° C. followed by washing three times in 2×SSC, 0.2% SDS at 40° C. for 30 minutes.

A suitable oligonucleotide probe to be used in the hybridization may be prepared on the basis of the DNA sequence shown in SEQ ID No. 3, or any of the DNA sequences shown in SEQ ID Nos. 1 or 2.

Immunological cross-reactivity

Antibodies to be used in determining immunological cross-reactivity may be prepared by use of a purified β-(1-6)-glucanase. More specifically, antiserum against the β-(1-6)-glucanase of the invention may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation (($NH_4)_2SO_4$), followed by dialysis and ion exchange chromatography, e.g. on DEAE-Sephadex. Immunochemical characterization of proteins may be done either by Outcherlony double-diffusion analysis (O. Outcherlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Coomassie staining

The gel is carefully removed from the glass plates and incubated on a slowly rotating shaking table in approximately 100 ml of the following solutions:

1) 30 min in 40% v/v ethanol; 5% v/v acetic acid
2) 30 min in 40% v/v ethanol; 5% v/v acetic acid+0.1% Commassie Brilliant Blue R250
3) Destaining in 30 min in 40% v/v ethanol; 5% v/v acetic acid until background is sufficiently reduced.
4) Finally the gel is incubated in preserving solution: 5% v/v acetic acid; 10% v/v ethanol; 5% v/v glycerol and air dried between two sheets of cellophane membrane.

Silverstaining

The gel is carefully removed from the glass plates and incubated on a slowly rotating shaking table in approximately 100 ml of the following solutions:

1) 30 min in 40% v/v ethanol; 5% v/v acetic acid
2) 20 min in 10% v/v ethanol; 5% v/v acetic acid
3) 20 min in 0.0057% w/v APS (0.25 mM)
4) 60 min in 0.1% w/v $AgNO_3$
5) For development, the gel is dipped in developer: 0.015% formaldehyde; 2% w/v $Na_2CO_3$ for 30–60 sec. Then the gel is incubated in a second round of developer until satisfactory staining of the proteins has been achieved (5–15 min.). Finally the gel is incubated in preserving solution: 5% v/v acetic acid; 10% v/v ethanol; 5% v/v glycerol and air dried between two sheets of cellophane membrane.

Media

YPD: 10 g yeast extract, 20 g peptone, $H_2O$ to 810 ml. Autoclaved, 90 ml 20% glucose (sterile filtered) added.

10 x Basal salt: 66.8 g yeast nitrogen base, 100 g succinic acid, 60 g NaOH, $H_2O$ ad 1000 ml, sterile filtered.

SC-URA: 90 ml 10 x Basal salt, 22.5 ml 20% casamino acids, 9 ml 1% tryptophan, $H_2O$ ad 806 ml, autoclaved, 3.6 ml 5% threonine and 90 ml 20% glucose or 20% galactose added.

SC-H broth: 7.5 g/l yeast nitrogen base without amino acids, 11.3 g/l succinic acid, 6.8 g/l NaOH, 5.6 g/l casamino acids without vitamins, 0.1 g/l tryptophan. Autoclaved for 20 min. at 121° C. After autoclaving, 10 ml of a 30% galactose solution, 5 ml of a 30% glucose solution and 0.4 ml of a 5% threonine solution were added per 100 ml medium.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan, and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar.

EXAMPLE 1

An *E. coli* library from *T. harzianum* consisting of approx. $10^6$ individual clones in 150 pools was constructed.

DNA was isolated from 20 individual clones from the library and subjected to analysis for cDNA insertion. The insertion frequency was found to be >90%. DNA from some of the pools was transformed into yeast, and 50–100 plates containing 200–500 yeast colonies were obtained from each pool.

Positive colonies were identified and isolated on agar. cDNA inserts were amplified directly from the yeast colony and characterized as described in the Materials and Methods section above. The full length sequences of the cDNA sequence encoding the β-(1-6)-glucanase is shown in SEQ ID No. 3.

EXAMPLE 2

Total DNA was isolated from a yeast colony and plasmid DNA was rescued by transformation of *E. coli* as described above. In order to express the pustulanase in Aspergillus, the DNA was digested with HindIII/XbaI, size fractionated on gel, and a fragment corresponding to the pustalanase gene was purified. The gene was subsequently ligated to HindIII/XbaI digested pHD414.

After amplification of the DNA in E. coli the plasmid pA1PU1 was transformed into Aspergillus oryzae as described above.

Test of A. oryzae transformants

Each of the transformants were tested for pustulanase activity as described above. Some of the transformants had pustulanase activity which was significantly larger than the Aspergillus oryzae background. This demonstrates efficient expression of the pustulanase in Aspergillus oryzae. The transformant with the highest pustalanase activity was selected and inoculated in a 500 ml shake flask with YPM media. After 3–5 days of fermentation with sufficient agitation to ensure good aeration, the culture broth was centrifuged for 10 minutes at 2000 g and the supernatant recovered.

EXAMPLE 3

Purification of pustulanase

The culture supernatant from fermentation of Aspergillus oryzae or A. niger expressing the pustulanase was centrifuged and filtered through a 0.2 μm filter to remove the mycelia. 35–50 ml of the filtered supernatant (5–50 mg recombinant enzyme) was ultrafiltrated in an Amicon ultrafiltration device with a 10 kDa membrane to achieve 10 fold concentration. This concentrate was diluted 100 times in 25 mM Tris pH 8.0 in two successive rounds of ultrafiltration in the same device. This ultrafiltrated sample was loaded at 1.5 ml/min on a Pharmacia XK16/10 Fast Flow Q Sepharose anion exchanger equilibrated in 25 mM Tris pH 8.0. After the sample was applied, the column was washed with two column volumes 25 mM Tris pH 8.0, and bound proteins ware eluted with a linear increasing NaCl gradient from 0 to 0.5 M NaCl in 25 mM Tris pH 8.0. 5 ml fractions are collected and assayed for pustulanase activity as described. The pustulanase was eluted at approximately 0.1 M NaCl. The pustulanase eluted from the column was not pure. Thus, the pustulanase containing fractions were pooled and concentrated by ultrafiltration in Amicon ultrafiltration device with a 10 kDa membrane to achieve 10 fold concentration. This concentrate was diluted 100 times in 10 mM sodium phosphate pH 6.8 in two successive rounds of ultrafiltration in the same device. This ultrafiltrated sample was loaded at 1 ml/min on a Pharmacia XK10/20 column packed with BioGel HTP (BioRad, USA) equilibrated in 10 mM sodium phosphate pH 6.8. After the sample has been applied, the column was washed with two column volumes 10 mM sodium phosphate pH 6.8 and bound proteins were eluted with a linear increasing concentration of sodium phosphate from 0.01 to 0.5 M. 5 ml fractions were collected and assayed for pustulanase activity. The pustulanase was to some degree retained on the column under these conditions, and the fractions containing pustulanase was concentrated in a Filtron Macrosep 10 kDa device to a final volume of 3 ml. This sample was loaded on a Pharmacia Superdex G75 column equilibrated in 0.25 M ammonium acetate pH 5.5 at a flow of 1 ml/min. 5 ml fractions were collected and assayed for pustulanase activity. The pustulanase eluted from this column was more than 95% pure as judged from SDS PAGE and used for the subsequent characterization.

EXAMPLE 4

Mw determination by SDS-PAGE Electrophoresis

SDS-PAGE electrophoresis was performed in a Mini-Leak 4 electrophoresis unit (Kem-En-Tec, Copenhagen) as a modified version of the Laemli procedure (Laemmli 1970; Christgau, Schierbeck et al. 1991). Briefly, the separation gel was cast with 12% acrylamide; 0.2% BIS acrylamide; 0.1% SDS; 0.375 M Tris pH 8.8; 0.04% APS (ammonium-persulphate) & 0.04% TEMED. After 6–15 hours polymerization the stacking gel was cast with 4.5% w/w Acrylamide; 0.075% BIS-acrylamide; 0.1% SDS; 66.5 mM Tris pH 6.8; 0.4% w/w APS (ammonium-persulphate) & 0.4% TEMED. The electrode chambers were filled with running buffer: 25 mM Tris-base; 0.192 M glycine & 0.05% SDS, whereafter the samples, containing sample buffer are loaded, and the gel was run at 2–4 mA/gel for over-night ring and 10–30 mA/gel for fast running, whereafter the gel was removed and stained by either commassie or silver staining as described above in the Materials and Methods section.

The apparent molecular weight was found to be about 50 kDa.

EXAMPLE 5 pI determination by Isoelectric focusing

Isoelectric focusing is carried out on Ampholine PAG plates pH 3.5–9.5 (Pharmacia, Upsala) on a Multiphor electrophoresis unit according to the manufactures instructions. After electrophoresis the gel was either commassie stained or silver stained as described above, except that prior to staining, the gel was incubated for 20 min in 20% TCA (Tri-chloro-acetic acid).

The apparent isoelectric point (pI) was found to be about 5.6.

EXAMPLE 6 pH optimum

Buffers of pH values between 2.5 and 8.0 were made by mixing 0.1 M Tri-sodium phosphate with 0.1 M citric acid. Pustulanase was diluted to ensure the assay response to be within the linear range of the assay. The substrate was a 0.5% solution of pustulan mixed 1:1 with the citrate/phosphate buffer to a final substrate concentration of 0.25% pustulan. 1 ml substrate in Eppendorf® 1.5 ml poly propylene tubes were added 10 μl of enzyme solution and incubated for 15 minutes in Eppendorf® temperature controlled Thermomixers before heat-inactivation of enzymes for 20 minutes at 95° C. in a separate Thermomixer. The concentration of reducing sugars after inactivation of enzyme were determined by reaction, in microtiter plates, with a PHBAH reagent comprising 0.15 g of para hydroxy benzoic acid hydrazide (Sigma H-9882), 0.50 g of potassium-sodium tartrate (Merck 8087) and 2% NaOH solution up to 10.0 ml. Glucose was used as a standard and blanks were subtracted.

For the pH optimum incubations took place at 30° C. For each pH value, three tubes were added enzyme and incubated before heat-inactivation, whereas one tube (the blank) was added enzyme and heat-inactivated immediately. The mean value of the three incubated samples was calculated and the blank value was subtracted. The value at optimal pH was defined as 100%.

The activity of pustulanase as a function of pH at 30° C. is shown in FIG. 1. It is seen that pustulanase has more than 40% activity between pH 4.0 and 6.0 and optimal activity at pH 5.0.

EXAMPLE 7

Temperature optimum

For the temperature optimum incubations took place as described above in pH 5.0 citrate/phosphate buffers. The temperatures ranged from 30° C. to 80° C. For each temperature three incubations were carried out and the mean calculated. Three blanks were produced by immediate heat-inactivation of enzymes and the mean was subtracted from the incubated sample values. The activity at the optimal temperature was defined as 100%.

Figure 2:
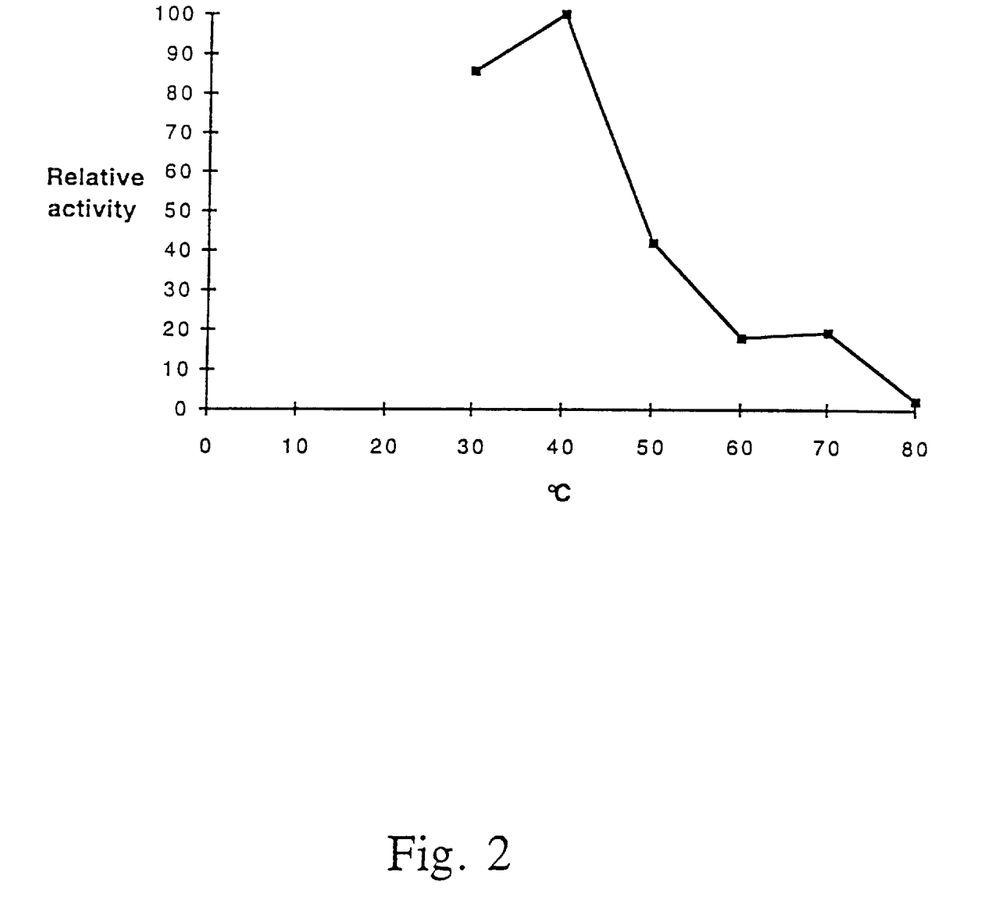
FIG. 2 shows the relative activity of the pustulanase of the invention as a function of temperature at pH 5.0.

The activity of pustulanase as a function of temperature at pH 5.0 is shown in FIG. 2. It is seen that pustulanase has more than 40% activity at temperatures below 50° C. and optimal activity at 30–40° C.

EXAMPLE 8

Kinetic parameters

Km and specific activity were determined by carrying out incubations at 30° C. for 15 minutes at pustulan concentrations (S) ranging from 0.1 to 1% in citrate/phosphate buffer pH 5.0. The reaction rate (v) was measured as the formation of reducing sugar/minute. Reducing sugars was determined by PHBAH reagent as described previously. Then S/v was depicted as a function of S, and linear regression analysis was carried out. The slope (=1/Vmax) and the intercept (Km/Vmax) was used to calculate the Km and the specific activity (=Vmax/E), where E was the amount of enzyme added. The specific activity was measured as U/mg of enzyme where 1 U=1 $\mu$mol reducing sugar/minute.

The specific activity of the pustulanase at 30° C. pH 5.0 was around 100 U/mg enzyme and Km around 0.3% pustulan.

EXAMPLE 9

Depolymerization of β-1,6 glucan

For gelfiltration chromatography 1 ml aliqouts of 1% solutions of pustulan were incubated with 20 $\mu$l of 0.2 mg/ml enzyme solution at 30° C. for 0, 1, 2, 4, and 24 hours before heat-inactivation. 25 $\mu$l of sample was injected into three TSK-columns (TosoHaas) in serie (PW G4000, PW G3000, PW G2500) and saccharides were eluted with 0.4 M acetate buffer pH 3.0 at 0.8 ml/min. Eluting saccharides were determined by a Shimadzu RI detector and collection of the data commenced 15 minutes after injection. Data were processed by Dionex software. Dextrans (from Serva) were used as molecular weight standards.

Figure 3:
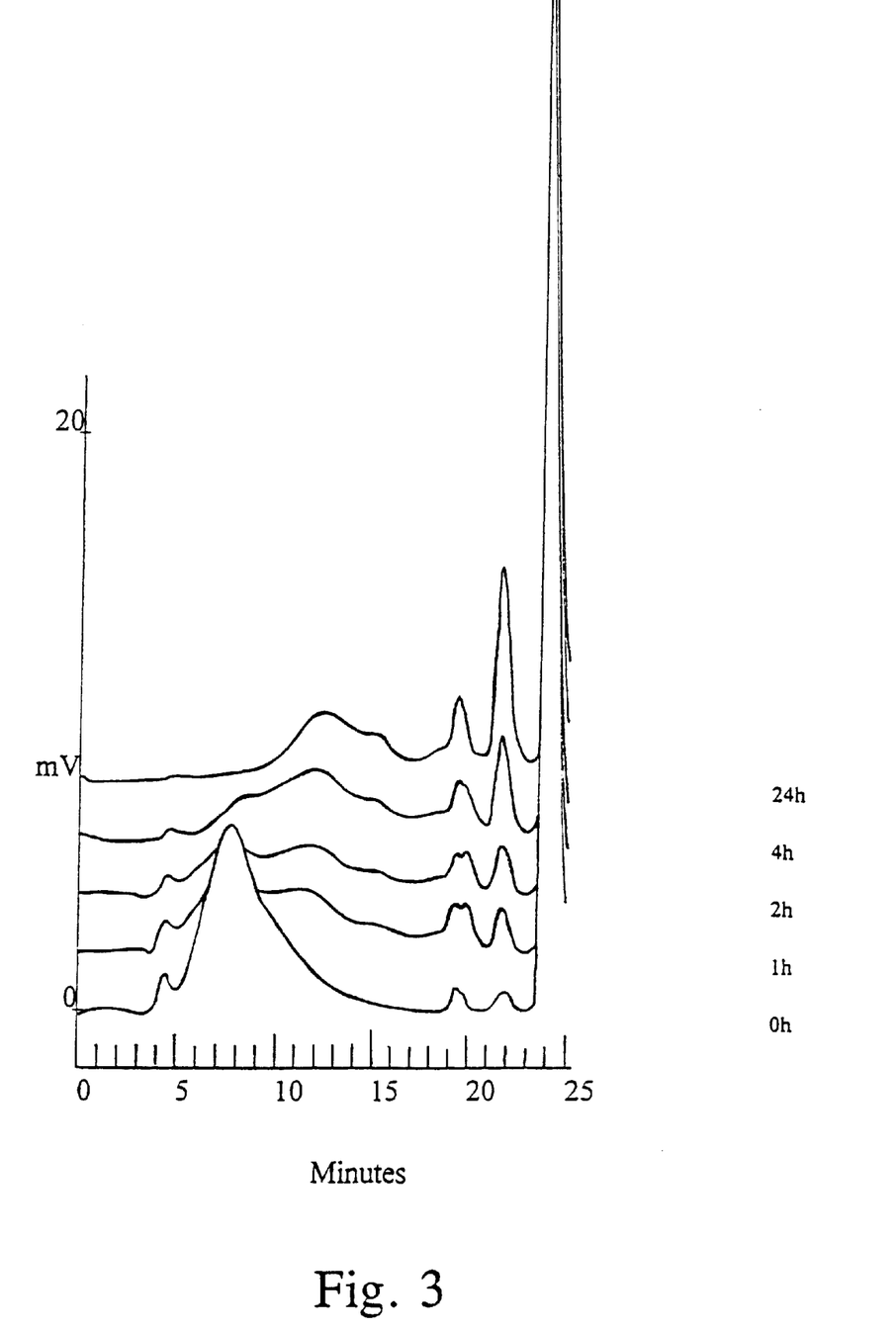
FIG. 3 shows the depolymerizing of pustulan by the pustulanase of the invention.

The pustalanase readily depolymerized the pustulan (see FIG. 3). These results are in accordance with the definition of an endo-β-1,6-glucanase activity (E.C. 3.2.1.75).

EXAMPLE 12

Hydrolysis trials on isolated yeast cell wall material 450 g of Bakers yeast, *Saccharomyces cerevisiae*, was suspended in 1350 g of water. A plasmolysis was carried out under stirring at 50° C. for 18 hours. 10 ml samples were taken at the time 0, 0.5 h, 1 h, 17 h, 17.5 h and at 18 h. The samples were centrifuged on a Labofuge centrifuge from Heraeus at 3400×g (equivalent to 4500 rpm on the used centrifuge) for 5 minutes. The reaction was followed by measurements on the supernatant of the osmolality using a Advanced Wide-Range Osmometer 3W2 (Advanced Instruments). A DUR REFRACTOMETER-Electronic (Schmidt Haensch) was used for testing of the dry matter content of these centrifugates. The data shown in table 1 was found:

TABLE 1

Data measured during the plasmolysis of bakers yeast

| Time (h) | Osmolality, mOSM/kg | °BRIX |
|---|---|---|
| 0 | 115 | 0.6 |
| 0.5 | 165 | 0.8 |
| 1 | 196 | 0.9 |
| 17 | 350 | 4.5 |
| 17.5 | 354 | 4.6 |
| 18 | 356 | 4.6 |

After 18 h the whole content was centrifuged at 4500 rpm using a Sorvall RC-3G refrigerated centrifuge for 30 minutes. 1475.8 g of supernatant and 227.3 g of solid phase was collected. The solid was suspended in 1475.8 g of water and centrifuged again at 4500 rpm using a Sorvall RC-3G refrigerated centrifuge for 30 minutes. Finally 266.1 g of washed cell wall material was collected.

A dry matter determination was carried out at 105° C. over night. A content of 22.8% w/w dry matter was found. This material is called isolated cell wall material from yeast.

A blank hydrolysis trial was carried out by use of 21.9 g of isolated wet cell wall material, which material was suspended ad 70 ml water in a 250 ml Erlenmeyer flask. pH was adjusted to pH=5.0 by use of 6 N HCl. The total content in the Erlenmeyer flask was adjusted to 100 ml. Samples were taken at t=1, 5, 10, 20, 30, 60, 90, 120, 180, 240 minutes. The samples were immediately centrifuged on a Labofuge centrifuge from Heraeus at 3400×g (equivalent to 4500 rpm on the used centrifuge) for 5 minutes. The reaction was followed by measurements on the supernatant of the osmolality using a Advanced Wide-Range Osmometer 3W2 (Advanced Instruments). The DUR REFRACTOMETER-Electronic was used for testing of the dry matter content of these centrifugates.

A hydrolysis trial was carried out as above but after the pH adjustment the total content in the Erlenmeyer flask was adjusted to 95 ml. After termostatting, approximately 2.5 mg pustulanase dissolved in 5 ml water was added. The hydrolysis reaction was carried out at 50° C. under magnet-stirring with the Erlemeyer flask placed in a water bath. Samples were taken and measured as above.

The data shown in table 2 was found for the blank hydrolysis and the pustulanase treated yeast cell wall material.

TABLE 2

Solubilizing and degrading effect of Pustulanase

| | Blank | | | Pustulanase treatment | | |
|---|---|---|---|---|---|---|
| Time min. | mOSM/ kg | ΔmOSM/ kg | °BRIX | mOSM/ kg | ΔmOSM/ kg | °BRIX |
| 1 | 20 | 0 | 0 | 48 | 0 | 0.1 |
| 5 | 20 | 0 | 0 | 48 | 0 | 0.1 |
| 10 | 21 | 1 | 0 | 49 | 1 | 0.14 |
| 20 | 21 | 1 | 0 | 52 | 4 | 0.20 |
| 30 | 22 | 2 | 0 | 54 | 6 | n.d |
| 60 | 23 | 3 | 0 | 60 | 12 | ta 0.24 |
| 90 | 24 | 4 | 0 | 65 | 17 | 0.30 |
| 120 | 26 | 6 | 0 | 69 | 21 | 0.34 |
| 180 | 28 | 8 | 0 | 77 | 29 | 0.42 |
| 240 | 30 | 10 | 0 | 83 | 35 | 0.48 | n.d. means: no data available.

REFERENCES

1. Aviv, H. & Leder, P. 1972. Proc. Natl. Acad. Sci. U.S.A. 69: 1408–1412.

2. Becker, D. M. & Guarante, L. 1991. Methods Enzymol. 194: 182–187.
3. Chirgwin, J. M., Przybyla, A. E., MacDonald, R. J. & Rutter, W. J. 1979. Biochemistry 18: 5294–5299.
4. Gubler, U. & Hoffman, B. J. 1983. Gene 25: 263–269.
5. Sambrook, J., Fritsch, E. F. & Maniatis, T. 1989. Molecular Cloning: A Laboratory Manual. Cold Spring Harbor Lab., Cold Spring Harbor, N.Y.
6. Sanger, F., Nicklen, S. & Coulson, A. R. 1977. Proc. Natl. Acad. Sci. U.S.A. 74: 5463–5467.
7. Pitson et al., Noncellolytic fungal β-glucanases: Their physiology and regulation. In Enzyme Microb. Technol., 1993, vol. 15, March
8. Reed and Nagodawithana, in Yeast Technology, Second Edition, pp. 372–380
9. Phaff, H. J., Enzymatic Yeast Cell Wall Degradation. In Food Proteins, Improvement through Chemical and Enzymatic Modification, edited by Feeney and Whitaker, Washington, 1977
10. Hamlyn et al., Efficient protoplast isolation from fungi using commercial enzymes. In Enzyme Microb. Technol., 1981, Vol. 3, October
11. Andrews and Asenjo, Enzymatic lysis and disruption of microbial cells. In Tibtech, October 1987, Vol. 5
12. Hudson, H. J. in "Fungal Biology", eds. Willis, A. J. and Sleigh, M. A., 1986, Edward Arnold (Publishers), Ltd.).
13. Dubourdieu et al., (1985), Investigations of an industrial β-D-Glucanase From *Trichoderma harzianum*, Carbohydrate Research, 144, 277–287.

We claim:

1. A DNA construct comprising a polynucleotide sequence encoding an enzyme exhibiting β-(1-6)-glucanase activity, wherein the polynucleotide comprises
   (a) the polynucleotide sequence of SEQ ID NO:3, or a fragment thereof encoding an enzymatically active polypeptide;
   (b) a polynucleotide encoding the amino acid sequence of SEQ ID NO:4; or
   (c) a polynucleotide which hybridizes to (a)–(b) under the following conditions: prehybridization for 1 h at about 40° C. in a solution of 5×SSC, 5×Denhart's, 50 mM sodium phosphate, pH 6.8, and 50 μg denatured sonicated calf thymus DNA, followed by hybridization in the same solution for 18 h at about 40° C., followed by washing three times in 2×SSC, 0.2% SDS at 40° C. for 30 min, wherein the polynucleotide encodes an enzyme exhibiting β-(1-6)-glucanase activity.

2. A DNA construct comprising the polynucleotide sequence of SEQ ID NO:1 or SEQ ID NO:2.

3. The DNA construct of claim 1, wherein the polynuclotide sequence is obtainable from a microorganism.

4. The DNA construct of claim 3, wherein the polynucleotide sequence is obtainable from a filamentous fungus or yeast.

5. The DNA construct of claim 4, wherein the polynucleotide sequence is obtainable from a strain of Trichoderma, Aspergillus, Penicillium, Fusarium, or Humicola.

6. The DNA construct of claim 5, wherein the polynucleotide sequence is obtainable from a strain of *Trichoderma harzianum*.

7. The DNA construct of claim 6, wherein the polynucleotide sequence is obtainable from a strain of *Trichoderma harzianum* CBS 243.71.

8. A recombinant expression vector comprising the DNA construct of claim 1.

9. A cell comprising the DNA construct of claim 1.

10. The cell of claim 9, wherein the cell is a eukaryotic cell.

11. The cell of claim 10, wherein the eukaryotic cell is a fungal cell.

12. The cell of claim 10, wherein the fungal cell is a yeast cell or a filamentous fungal cell.

13. The cell of claim 12, wherein the cell belongs to a strain of Aspergillus.

14. The cell of claim 13, wherein the strain is *Aspergillus niger* or *Aspergillus oryzae*.

15. A method for producing an enzyme exhibiting β-(1-6)-glucanase activity, comprising (a) culturing the cell of claim 9 under conditions permitting the production of the enzyme, and (b) recovering the enzyme.

* * * * *